(12) United States Patent
Cho et al.

(10) Patent No.: US 7,959,862 B2
(45) Date of Patent: Jun. 14, 2011

(54) MICROFLUIDIC DEVICE AND METHOD FOR CONCENTRATION AND LYSIS OF CELLS OR VIRUSES

(75) Inventors: Yoon-kyoung Cho, Yongin-si (KR); Jeong-gun Lee, Yongin-si (KR); Sung-young Jeong, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 774 days.

(21) Appl. No.: 11/610,938

(22) Filed: Dec. 14, 2006

(65) Prior Publication Data

US 2007/0134809 A1    Jun. 14, 2007

(30) Foreign Application Priority Data

Dec. 14, 2005    (KR) .................. 10-2005-0123161

(51) Int. Cl.
G01N 15/06    (2006.01)
(52) U.S. Cl. ... 422/68.1; 422/82.01; 422/78; 435/287.2; 435/288.5; 435/288.7; 435/306.1; 435/372; 436/63; 436/149
(58) Field of Classification Search .................. None
See application file for complete search history.

(56) References Cited

U.S. PATENT DOCUMENTS 6,221,673 B1 *  4/2001  Snow et al. ................. 436/149
6,815,209 B2 *  11/2004  Baeummer et al. ........... 436/63
2003/0134416 A1 *  7/2003  Yamanishi et al. ........... 435/372
2004/0018611 A1    1/2004  Ward et al.
2005/0221341 A1 *  10/2005  Shimkets et al. ................. 435/6

FOREIGN PATENT DOCUMENTS

WO    0212896    2/2002

OTHER PUBLICATIONS

Invitrogen manual, Dynabeads Product information.*
Mohit D. Dhawan et al.; Development of laser-induced cell lysis system; Anal Bioanal Chem (2002) 374: 421-426.
European Search Report for application No. 06126171.5 dated Apr. 23, 2007.
Microship Laser-Induced Fluorescence Detection of Proteins at Submicrogram per Milliliter Levels Mediated by Dynamic Labeling under Pseudonative Conditions; Braden C. Giordano,†,‡ Lianji Jin,† Abigail J. Couch,† Jerome P. Ferance,† and James P. Landers,†,§; Anal. Chem. 2004, 76, 4705-4714.

* cited by examiner

Primary Examiner — Sally A Sakelaris
(74) Attorney, Agent, or Firm — Cantor Colburn LLP

(57) ABSTRACT

A microfluidic device for the concentration and lysis of cells or viruses and a method of concentrating and lysing cells or viruses using the microfluidic device include: magnetic beads, a reaction chamber in which the magnetic beads are accommodated and a laser source. The reaction chamber includes a plurality of electrodes which cross each other and are separated by a dielectric to generate an electric field and a vibrating part agitating the magnetic beads in the chamber. The laser source radiates a laser onto the magnetic beads in the reaction chamber.

25 Claims, 12 Drawing Sheets

(W,P):(25,25)

(W,P):(25,9)

(W,P):(5,25)

(W,P):(12,25)

Trapped S.M.

Trapped magnetic beads

US 7,959,862 B2

MICROFLUIDIC DEVICE AND METHOD FOR CONCENTRATION AND LYSIS OF CELLS OR VIRUSES

This application claims priority to Korean Patent Application No. 10-2005-0123161, filed on Dec. 14, 2005, and all the benefits accruing therefrom under 35 U.S.C. §119, the contents of which in its entirety are herein incorporated by reference.

BACKGROUND OF THE INVENTION

1. Field of the Invention

The present invention relates to a microfluidic device, and more particularly to a microfluidic device for concentrating and lysing cells or viruses in one chamber and a method of concentrating and lysing cells or viruses using the microfluidic device.

2. Description of the Related Art

A biological analysis process including pathogen detection or molecular diagnosis is composed of target cell separation, cell concentration, biomolecule separation, biomolecule amplification, a hybridization reaction and detection.

Research has been performed on a lab-on-a-chip ("LOC") in which a series of biologic analysis processes can be performed quickly and automatically on a microchip.

An LOC includes a microfluidic device to perform a biological analysis process. The microfluidic device includes an inlet, an outlet, a reaction chamber and a microchannel connecting the inlet, the outlet and the reaction chamber. The microfluidic device is equipped with a micropump for transferring fluid, a micromixer for mixing fluid, a microfilter for filtering fluid, etc., in addition to the microchannel.

Examples of conventional devices for integrating a biologic analysis process can be found on the Internet.

A conventional integrated system includes a cell counting chamber, a cell sorting chamber, a DNA extraction chamber, a PCR amplification chamber and a detection chamber. The chambers are connected in sequence by a channel. Each of the chambers includes a valve and a pump.

However, when simply connecting devices which carry out biological analysis processes, it is difficult to integrate the devices as one device due to the need for a plurality of valves and microfluidic controllers. Further, the integrated device has a large volume and is expensive.

Therefore, in order to reduce the size of an LOC, as many biological analysis processes as possible should be performed in a single chamber.

BRIEF SUMMARY OF THE INVENTION

The present invention provides a microfluidic device for the concentration and lysis of cells or viruses in a single chamber.

The present invention also provides a method of concentrating and lysing cells or viruses using the microfluidic device.

According to an exemplary embodiment of the present invention there is provided a microfluidic device for concentration and lysis of cells or viruses, including: magnetic beads; a reaction chamber in which the magnetic beads are accommodated, including a plurality of electrodes crossing each other and separated by a dielectric to generate an electric field; a vibrating part agitating the magnetic beads in the reaction chamber; and a laser source which radiates a laser onto the magnetic beads in the reaction chamber.

According to another exemplary of the present invention, there is provided a method of concentrating and lysing cells or viruses using the above described microfluidic device including: applying a voltage to the electrodes and generating a non-uniform electric field in the reaction chamber; flowing a fluid which has cells or viruses into the reaction chamber; flowing a fluid which has the magnetic beads into the reaction chamber; and radiating a laser onto the magnetic beads.

By using the microfluidic device and the above described method, cells or viruses can be concentrated and lysed effectively. Furthermore, the concentration and lysis can be performed in a single chamber.

BRIEF DESCRIPTION OF THE DRAWINGS

The above and other aspects, features and advantages of the present invention will become more apparent by describing in more detail exemplary embodiments thereof with reference to the attached drawings in which.

DETAILED DESCRIPTION OF THE INVENTION

Figure 1:
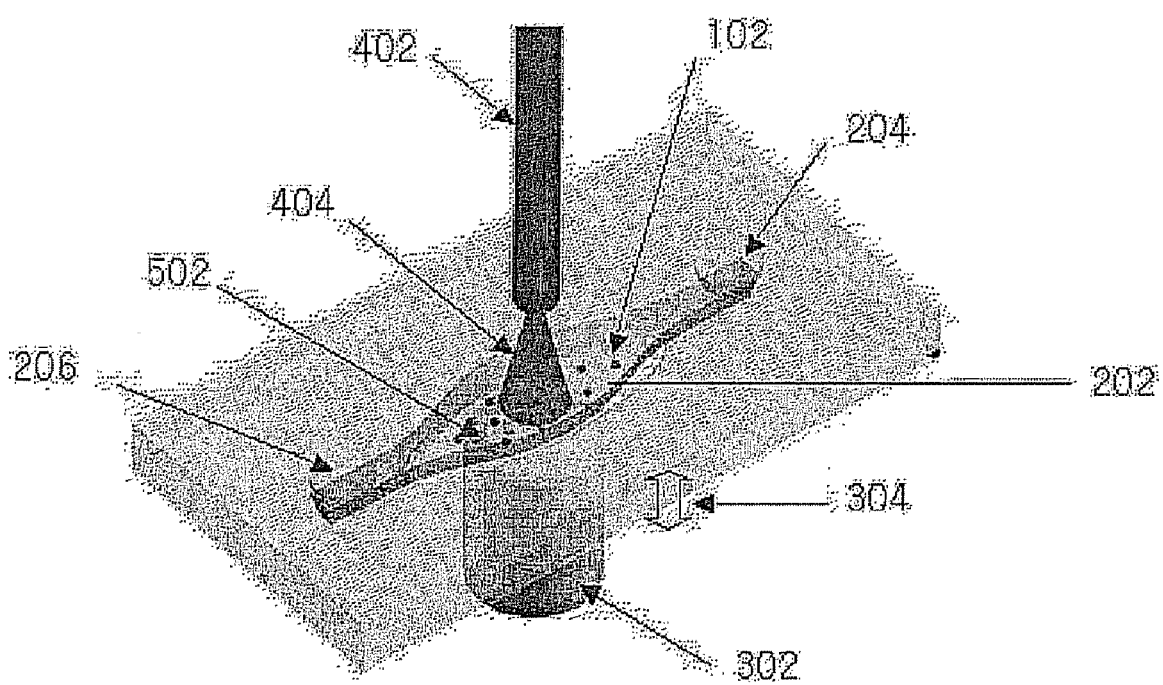
FIG. 1 is a perspective view of a schematic diagram of a microfluidic device according to an exemplary embodiment of the present invention.

The present invention will now be described more fully with reference to the accompanying drawings, in which exemplary embodiments of the present invention are shown. The present invention may, however, be embodied in many different forms and should not be construed as being limited to the exemplary embodiments set forth herein; rather, these exemplary embodiments are provided so that this disclosure will be thorough and complete, and will fully convey the concept of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will be described in detail with reference to the accompanying drawings.

FIG. 1 is a schematic diagram of a microfluidic device according to an exemplary embodiment of the present invention. The microfluidic device can be used for the concentration and lysis of cells or viruses.

Referring to FIG. 1, the microfluidic device includes magnetic beads 102; a reaction chamber 202, in which the magnetic beads 102 are accommodated, equipped with electrodes separated by a dielectric (not shown) to generate an electric field; a vibrating part 302 agitating the magnetic beads 102 in the reaction chamber 202; and a laser generator 402 supplying a laser 404 to the magnetic beads 102 in the reaction chamber 202.

In an exemplary embodiment of the present invention, the size of the magnetic beads may be about 50 nm to about 1,000 µm, for example 1-50 µm. If the size of the particles is less than 50 nm, physical and mechanical impact powers of the particles are not sufficient to occur. Also, if the size of the magnetic beads is greater than 1,000 µm, the magnetic beads are too large to be effective in a lab-on-a-chip ("LOC"). The magnetic beads 102 may be a mixture of magnetic beads having two or more sizes. In other words, the magnetic beads 102 may include magnetic beads of one size or a mixture of magnetic beads of different sizes.

In an exemplary embodiment of the present invention, the magnetic beads 102 can be any type of beads which are magnetic. Particularly, they may have one or more materials selected from the group consisting of ferromagnetic metals such as Fe, Ni, and Cr and oxides thereof.

In another exemplary embodiment of the present invention, the magnetic beads 102 may include a polymer, an organic material, silicon, or glass coated with ferromagnetic metals.

In an exemplary embodiment of the present invention, an external surface defining the magnetic beads 102 may have a negative charge, and thus DNA does not stick thereto. Since DNA has a negative charge, DNA does not stick to the surface of the magnetic beads 102 due to a repulsive force if the surface also has a negative charge. If DNA sticks to the surface of the magnetic beads 102, it is difficult to refine DNA because a cell has to be destroyed, and thus it becomes difficult to separate the magnetic beads 102 and DNA.

In an exemplary embodiment of the present invention, a surface functional group of the magnetic beads 102 may be hydrophilic. The amplification efficiency of DNA obtained from the lysed cells may vary according to a functional group on surface of the magnetic beads 102. The amplification efficiency of DNA increases as a functional group of the magnetic beads surface becomes more hydrophilic. The functional group may be negatively charged and have a carboxy radical or a derivative thereof. The derivative may be iminodiacetic acid ("IDA"), ethylene diamine tetraacetic acid ("EDTA"), citric acid, or polycarboxylic acid.

The reaction chamber 202 includes electrodes separated by a dielectric (not shown) to generate an electric field. The reaction chamber 202 may have an inlet port 204 through which fluid can flow in and an outlet port 206 through which fluid can flow out. The fluid may contain the magnetic beads 102, cells, or viruses 502.

In an exemplary embodiment of the present invention, a crossing electrode portion includes rows of two or more electrodes disposed perpendicularly to fluid flow. Odd rows of electrodes can be connected to a metal pad through a metal line and even rows of electrodes can be connected to another metal pad through another metal line.

In an exemplary embodiment of the present invention, the neighboring even and odd rows of electrodes may overlap each other.

In an exemplary embodiment of the present invention, the electrodes of one odd row are connected to a metal pad through a single metal line. The electrodes of one even row may also be connected to a metal pad through a single metal line. The metal pad and the metal line can be composed of any metal. For example, the metal can be selected from the group of gold, copper, and platinum, and may be a biocompatible metal such as gold, which is desirable for cells or bio-mass.

In an exemplary embodiment of the present invention, an interval between an electrode of an odd row and an electrode of an even row is about 10 μm to about 100 μm. Intervals between adjacent electrodes of an odd row and between adjacent electrodes of an even row are about 10 μm to about 100 μm. The thickness of the electrodes can be about 0.1 μm to about 100 μm, for example, between about 50 μm and about 100 μm.

In an exemplary embodiment of the present invention, the electrodes can be columnar, for example, cylindrical or a square pillar shape. Alternatively, the electrodes can be flat type electrodes. However, the shape of the electrodes which can be used in exemplary embodiments of the present invention is not limited to the above examples, and the electrodes can have any form.

In an exemplary embodiment of the present invention, the angle between the electrode and a substrate in which the electrode is adhered to is from about 50° to about 120°. If the electrodes have a square pillar form, they can have an inversed circular truncated cone, and if the electrodes have a cylindrical form, they can have an inversed quadrangular truncated pyramid shape.

In an exemplary embodiment of the present invention, the electrodes can be gold coated on a metal. The metal may be nickel, for example.

In an exemplary embodiment of the present invention, the chamber can be composed of any material, such as glass, silicon, pyrex, quartz, or SU-8. The material forming the chamber may be a transparent material such as glass, pyrex, quartz, or SU-8.

In an exemplary embodiment of the present invention, the chamber has a lower substrate and an upper substrate. The electrodes can be disposed on both the lower substrate and the upper substrate. A chamber including a lower substrate and an upper substrate can be manufactured by making a lower substrate and an upper substrate separately and then joining them, but the present invention is not limited to this example. To join the base substrate and the upper substrate, any bonding method which is known to those of ordinary skill in the art can be used. For example, an adhesive tape which is commercially available from 3M can be used. In an exemplary embodiment of the present invention, rows of the electrodes disposed on the lower substrate and rows of the electrodes disposed on the upper substrate correspond to each other. The electrodes of the odd rows on the lower substrate and the electrodes of the even rows on the upper substrate are connected to the same metal pad. The electrodes of the even rows on the lower substrate and the electrodes of the odd rows on the upper substrate can be connected to the same metal pad.

Figure 2A:
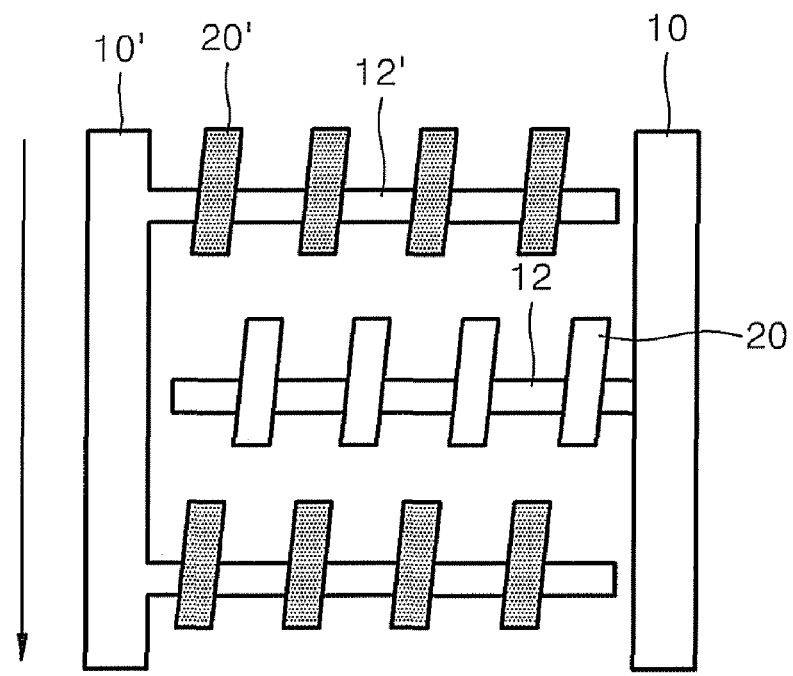
FIGS. 2A and 2B are diagrams illustrating electrode structures according to an exemplary embodiment of the present invention.
Figure 2B:
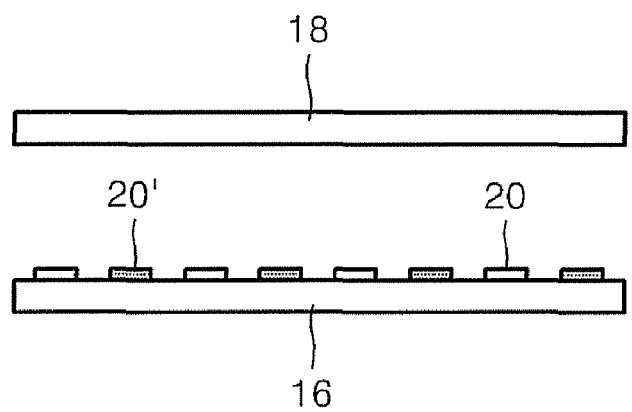
Figure 2C:
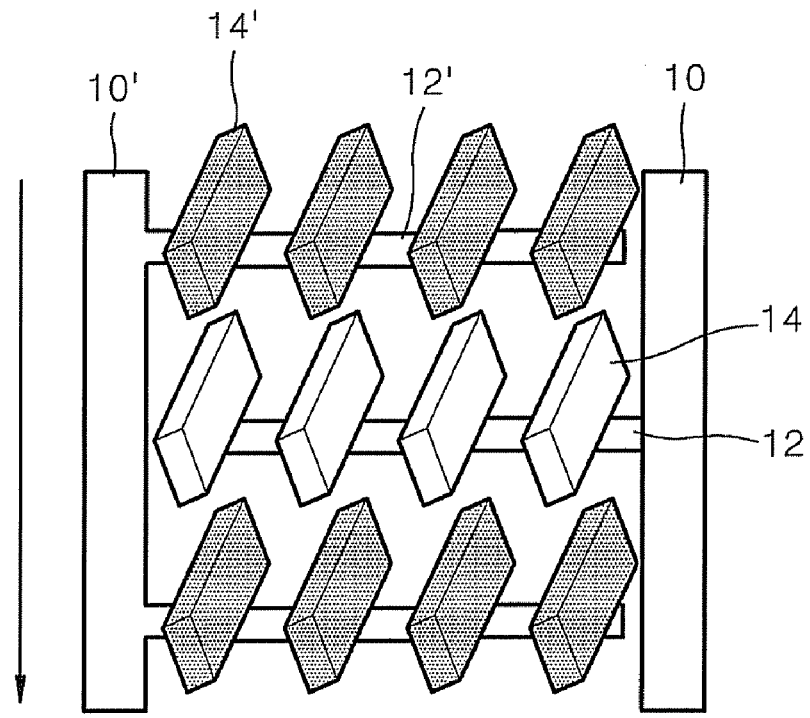
FIGS. 2C and 2D are diagrams illustrating electrode structures according to another exemplary embodiment of the present invention.
Figure 2D:
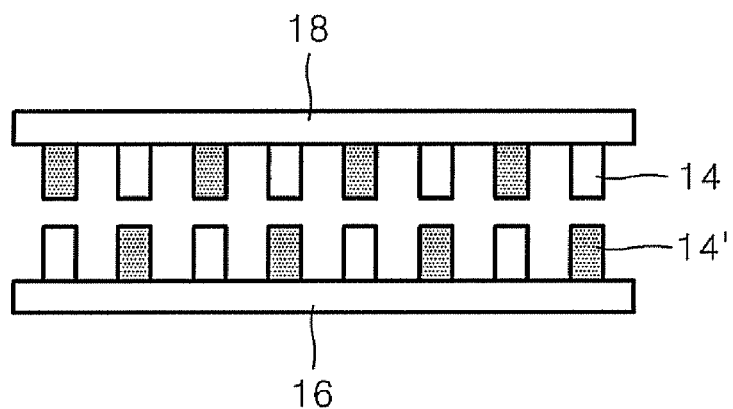

FIGS. 2A and 2B are diagrams illustrating electrode structures according to an exemplary embodiment of the present invention. FIGS. 2C and 2D are diagrams illustrating electrode structures according to another exemplary embodiment of the present invention.

Referring to FIG. 2A, rows of metal plates 20 and 20' are disposed perpendicularly to the flow direction of a fluid indicated by the arrow in FIG. 2A. Each of the rows includes four of either of the metal plates 20 or 20'. Moreover, the metal plates 20' of odd rows are connected to a metal pad 10' through a metal line 12'. The metal plates 20 of even rows are connected to another metal pad 10 through a metal line 12. As shown in FIG. 2B, the device includes an upper substrate 18 and a lower substrate 16, and the metal plates 20, 20' are disposed on the lower substrate 16. The metal plates 20, 20' can be disposed on the surface of the upper, or both on the lower substrate 16 and on the upper substrate 18.

Referring to FIG. 2C, rows of metal posts 14 and 14' are disposed perpendicularly to the flow direction of the fluid indicated by the arrow in FIG. 2C. Each of the rows includes a plurality of either of metal posts 14 or 14'. Moreover, the metal posts 14' of odd rows are connected to a metal pad 10' through a metal line 12', and the metal posts 14 of even rows are connected to another meal pad 10' through a metal line 12. As shown in FIG. 2D, the device includes an upper substrate 18 and a lower substrate 16. The metal posts 14 and 14' are disposed on both the lower substrate 16 and the upper substrate 18.

In an exemplary embodiment of the present invention, the vibrating part 302 may include an ultrasonic cleaner, a vibrating unit which operates in response to a magnetic field, a vibrating unit which operates in response to an electric field, a mechanical vibrating unit such as a vortex, etc., or piezoelectric materials. The vibrating part 302 can be attached to a cytolysis chamber, and can be any device which can vibrate a mixture of cells and micro magnetic beads.

The vibration direction of the vibrating part 302 can be any direction, for example, a vertical direction or a horizontal direction. Referring to FIG. 1, the vibrating part 302 vibrates the reaction chamber 202 including the magnetic beads 102 in a vertical direction 304.

In an exemplary embodiment of the present invention, the laser 404 can be a pulse laser or a continuous wave laser.

If the output power of the laser is too low, a laser ablation phenomenon cannot occur efficiently. The output power can be more than 10 mW for a continuous wave and more than 1 mJ/pulse for a pulse laser. The output power of the pulse laser may be 3 mJ/pulse or greater, and the output power of the continuous wave laser may be 100 mW or greater. If the output power of the continuous wave laser is less than 10 mW or the output power of the pulse laser is less than 1 mJ/pulse, not enough energy to destroy cells is transmitted.

In an exemplary embodiment of the present invention, the laser generates a specific wavelength band which the magnetic beads 102 can absorb. The laser may generate light in a wavelength band of 400 nm or greater, for example, in a wavelength band of about 750 nm to about 1300 nm. This is because a problem of denaturalization or damage to DNA occurs with a wavelength of less than 400 nm. Moreover, the laser generator 402 can generate one or more wavelength bands. That is, the laser 404 can have one wavelength in the above wavelength range or two or more different wavelengths.

A method of concentration or lysis of cells or viruses using the microfluidic device according to an exemplary embodiment of the present invention will now be described.

When a cell concentration in which dielectrophoresis ("DEP") is performed by an electrode portion and a cytolysis in which a laser and magnetic beads are sequentially used, several problems can arise.

For example, if a magnetic bead containing solution is injected into a reaction chamber after concentrating cells in the reaction chamber, the following problems are likely to occur: the loss of the concentrated sample; difficulty of control of a small chamber volume; and the generation of bubbles during the injection of an additional solution.

Figure 8A:
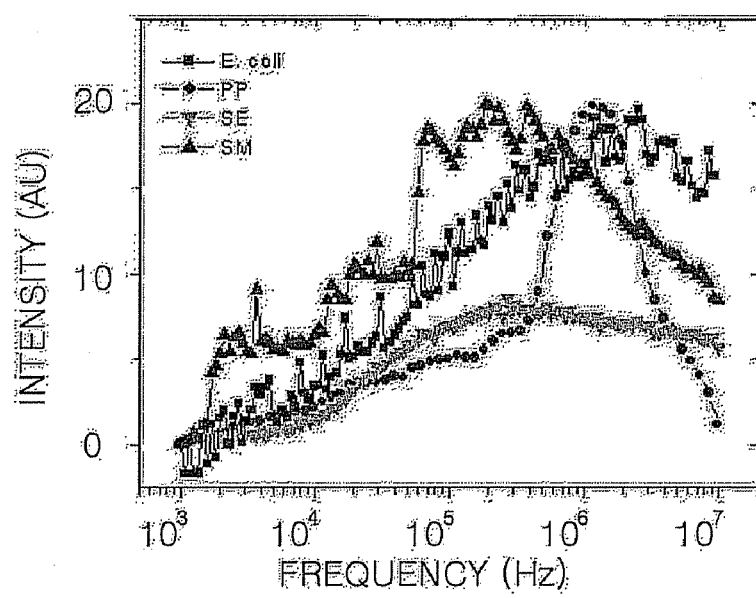
FIG. 8A is a diagram illustrating the trapping efficiency of various bacteria according to the frequency of an applied voltage.
Figure 8B:
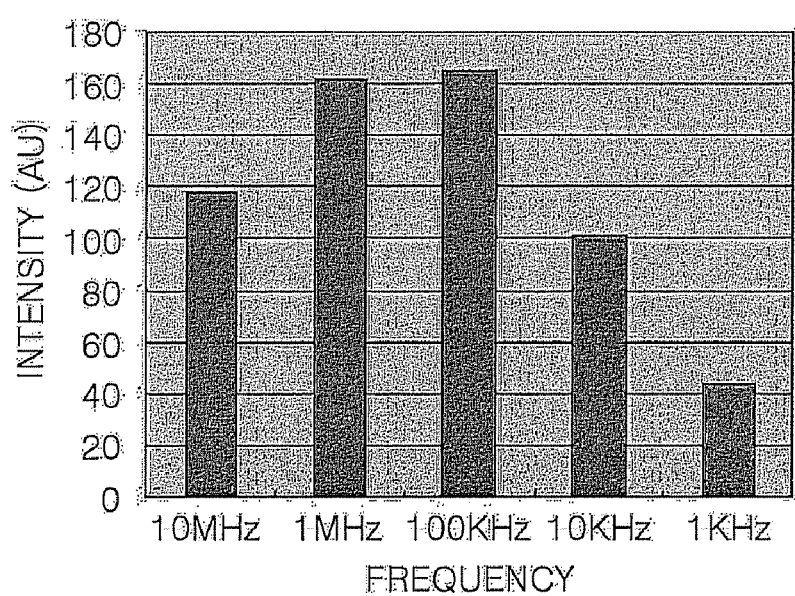
FIG. 8B is a diagram illustrating the trapping efficiency of magnetic beads according to the frequency of an applied voltage.

It has been confirmed by the inventors of the present invention that the magnetic beads used for laser lysis had a similar DEP condition to bacteria and that the magnetic beads and the bacteria were captured in an electrode with similar applied voltage frequency, referring to FIGS. 8A and 8B. The optimum conditions for a concentration and lysis method of cells or viruses were confirmed using this information.

Figure 7:
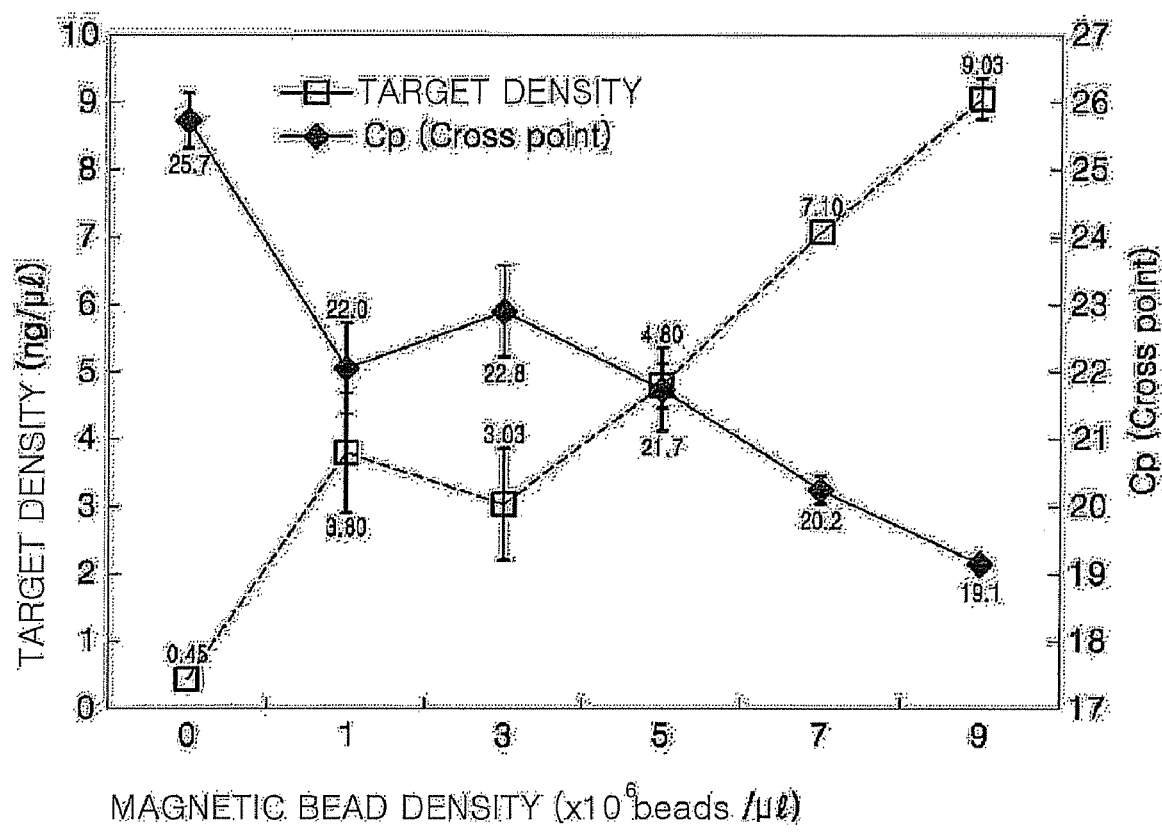
FIG. 7 is a graph showing the results of a polymerase chain reaction (PCR) of DNA extracted from *E. coli* cells according to magnetic bead density.

First, when that magnetic bead solution and cells were mixed in the reaction chamber 202 (FIG. 1), the loss of the magnetic bead solution was significant (not illustrated). This method is not desirable since a higher magnetic bead density ensures better cytolysis efficiency, as illustrated in FIG. 7.

Figure 10A:
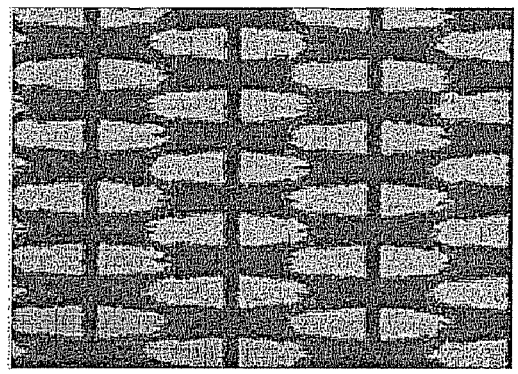
FIG. 10A is a photograph taken after flowing magnetic beads through a reaction chamber at a rate of 50 µl/min for one minute.
Figure 10B:
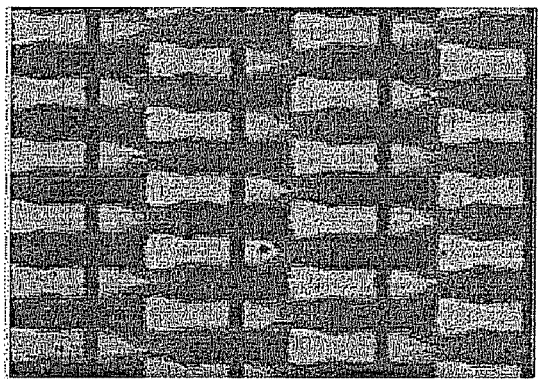
FIG. 10B is a photograph taken after flowing *Streptococcus mutans* at a rate of 250 µl/min for one second after flowing the magnetic beads through the reaction chamber.
Figure 10C:
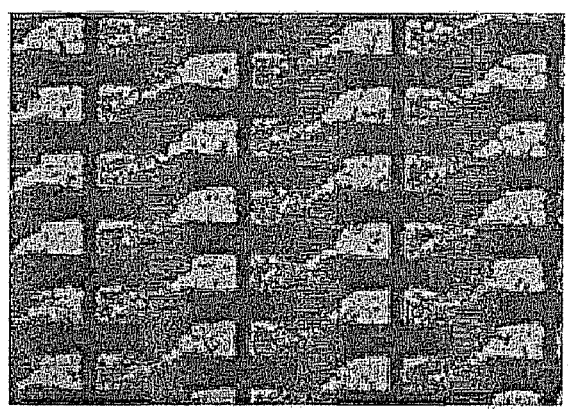
FIG. 10C is a photograph taken after flowing *Streptococcus mutans* at a rate of 250 µl/min for 60 seconds after flowing the magnetic beads through the reaction chamber.

Moreover, if cells are concentrated in the reaction chamber 202 after capturing a magnetic bead containing solution, the captured magnetic beads 102 are washed out if a sample solution is flowed at a fast rate for cell concentration, as illustrated in FIGS. 10B and 10C. As the speed of the flow increases, cell concentration increases but cytolysis efficiency decreases because magnetic beads 102 which have been captured are removed, as illustrated in FIG. 7.

Figure 11A:
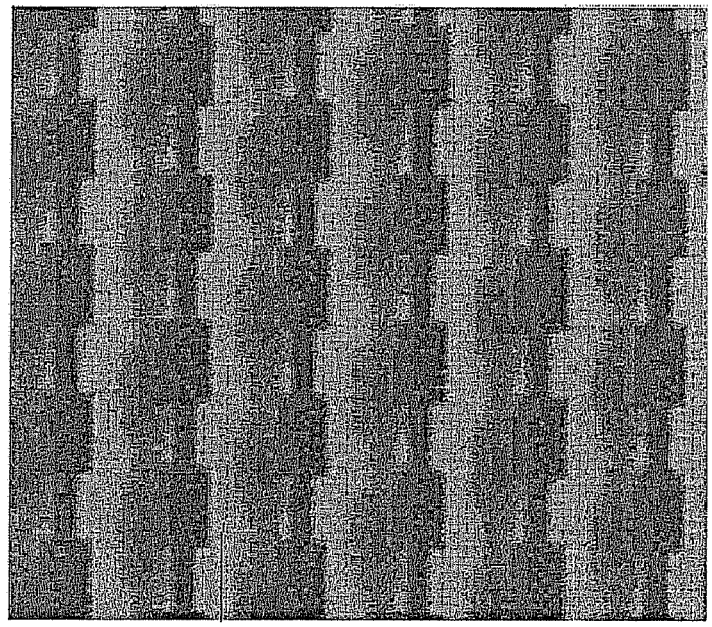
FIG. 11A is a photograph taken after flowing *Streptococcus mutans* at a rate of 250 µl/min for four minutes through the reaction chamber.
Figure 11B:
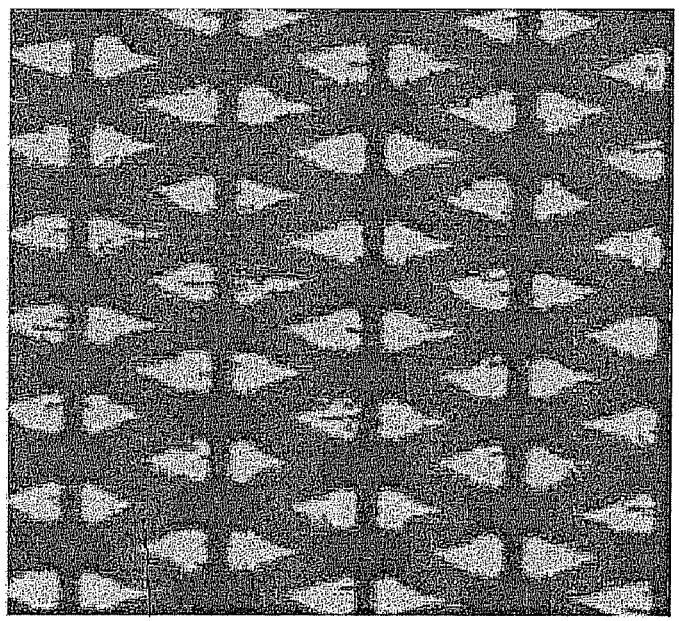
FIG. 11B is a photograph taken after flowing magnetic beads at a rate of 50 µl/min for one minute after flowing the *Streptococcus mutans* through the reaction chamber.

On the other hand, when removing a small amount of the magnetic bead containing solution after capturing cells in the reaction chamber 202, both the cells and the magnetic beads 102 were captured very effectively in an electrode, as indicated in FIGS. 11A and 11B.

Therefore, a concentration and lysis method of cells or viruses using the microfluidic device of FIG. 1 according to an exemplary embodiment of the present invention may include: applying a voltage to a crossing electrode portion and generating a non-uniform electric field in the reaction chamber 202; flowing a fluid which has cells or viruses into the reaction chamber 202; flowing a fluid which has magnetic beads 102 into the reaction chamber; and radiating a laser 404 onto the magnetic beads 102.

In an exemplary embodiment of the present invention, the applied voltage can have a magnitude of about 1 V to about 100 V and a frequency of about 100 Hz to about 100 MHz.

As described above, after generating a non-uniform electric field in the reaction chamber 202 and flowing the fluid which has the cells or viruses into the reaction chamber 202, the cells or viruses are captured through DEP in the electrode portion of the microfluidic device according to an exemplary embodiment of the present invention and are concentrated as a result.

Moreover, if the fluid having the magnetic beads 102 flows into the reaction chamber 202 after generating the non-uniform electric field in the chamber 202, the magnetic beads 102 are also captured through DEP in the electrode portion of the microfluidic device according to an exemplary embodiment of the present invention.

In an exemplary embodiment of the present invention, the inflow rate of the fluid can be 0.1 mm/sec or greater, for example, 1 mm/sec or greater.

When the laser 404 is radiated onto the magnetic beads 102, the laser ablation phenomenon occurs. Thus, an impulse wave, vapor pressure and heat are delivered to the cell surfaces, and the physical impacts thereof are applied simultaneously. The magnetic beads 102 heated by the laser 404 raise the temperature of the sample solution, and the hot magnetic beads 102 directly lyse cells or viruses. The magnetic beads 102 in the sample solution do not exist as simple heat transfer bodies but thermally, mechanically and physically affect the cells' surfaces, thus effectively destroying the cell surfaces.

Denaturalized protein and cell debris adhere to the magnetic beads 102, which can be removed using a magnetic force or gravity. This allows a remarkable improvement in PCR analysis by lowering a detection limit, drastically reducing DNA extraction time through the reduction of DNA extraction process into one step, and increasing a signal amplitude. It takes only 40 seconds to lyse cells using the micro magnetic beads 102 and the laser 404.

In an exemplary embodiment of the present invention, the sample solution can be selected from the group consisting of spittle, urine, blood, blood serum and cell broth. The sample solution can include materials having nucleic acids such as animal cells, plant cells, bacteria, viruses, and phages. When the sample solution includes animal cells, plant cells, bacteria, or viruses, the conductivity of the sample solution can be less than 30 mS/m.

Figure 12:
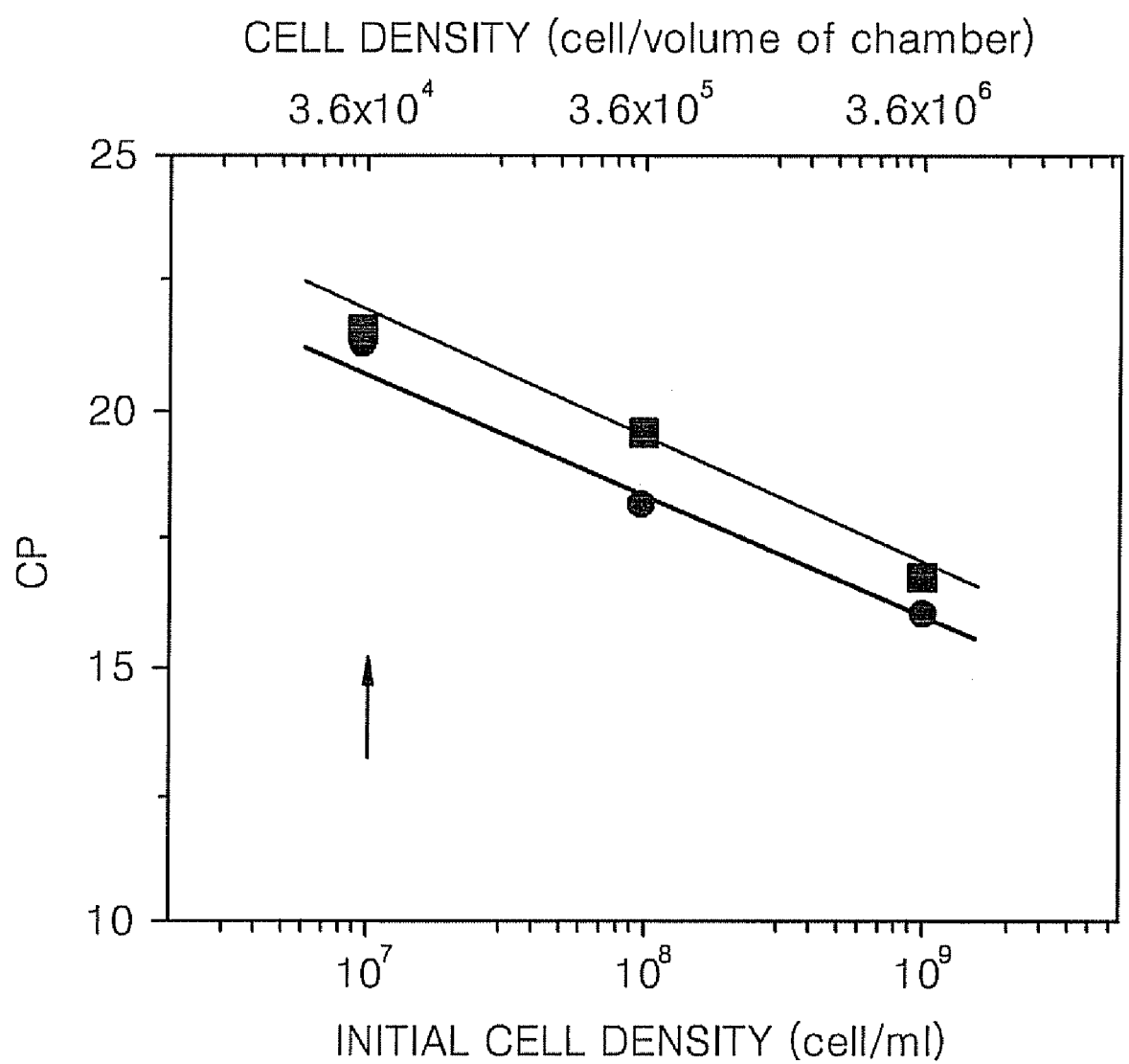
FIG. 12 is a graph showing the results of taking a solution from a chip and performing real-time PCR when: performing cytolysis with only a laser step and not a concentration step, using a chip for cytolysis; performing cytolysis with only a laser step and not a concentration step, using a chip for cell concentration in which a metal electrode is patterned on glass; and performing cytolysis with a laser step after concentration using a chip for cell concentration in which a metal electrode is patterned.

The method according to the present exemplary embodiment can obtain excellent effects, equivalent to those obtained using 100 or more times the DNA when performing only cytolysis with a laser, as can be seen in Table 1 below and FIG. 12.

The present invention will now be described in greater detail with reference to the following examples. The following examples are for illustrative purposes only and are not intended to limit the scope of the invention.

EXAMPLE 1

<Manufacture of Microfluidic Device>

Figure 3A:
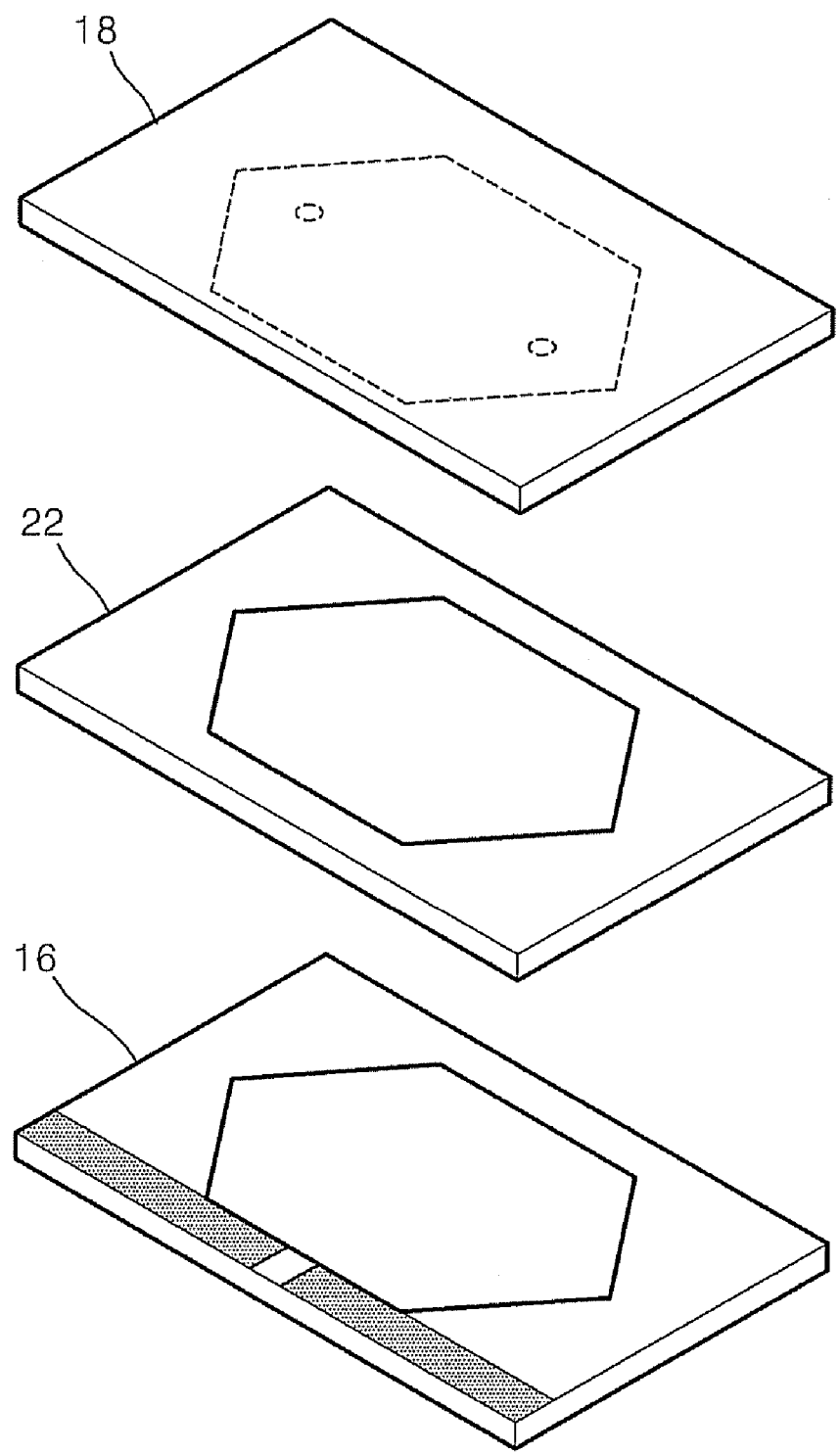
FIG. 3A is an exploded perspective view of a reaction chamber used in an exemplary embodiment of the present invention.
Figure 3B:
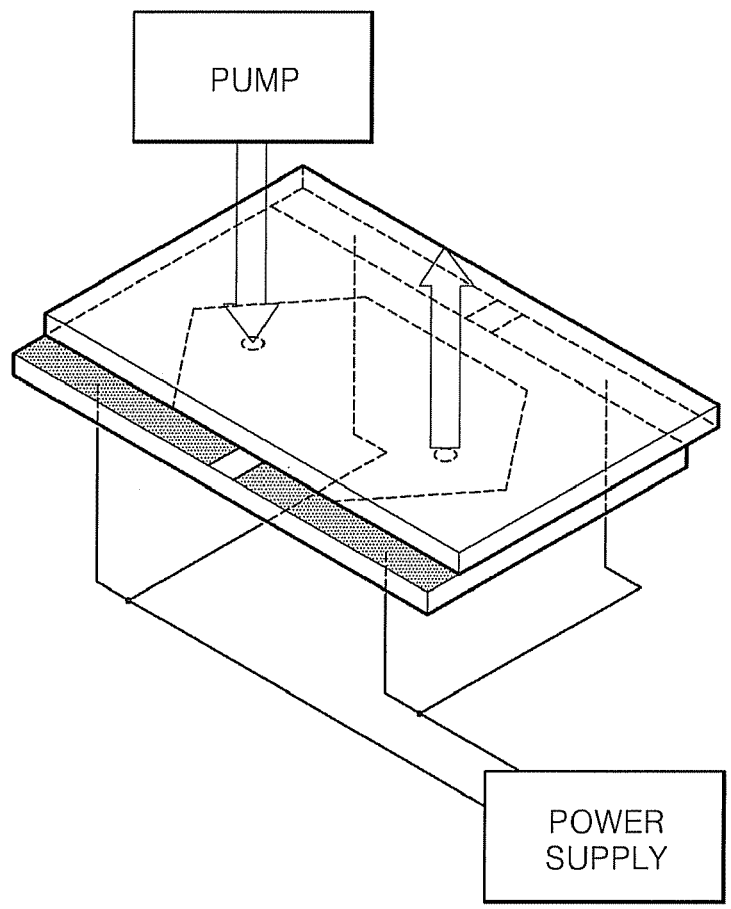
FIG. 3B is a perspective view of a reaction chamber used in an exemplary embodiment of the present invention.

FIGS. 3A and 3B are respectively an exploded perspective view and a perspective view of a reaction chamber which was prepared. Referring to FIG. 3A, the reaction chamber was formed by connecting an upper substrate 18 and a lower substrate 16 on which an array of gold pillars was formed, with 3M adsorption tape 22 (commercially available from 3M, U.S.) FIG. 3B illustrates the manufactured reaction chamber, through which a fluid flows by entering an inlet port and exiting an outlet port using a pump, and to which electric power is supplied through metal pads.

Figure 4:
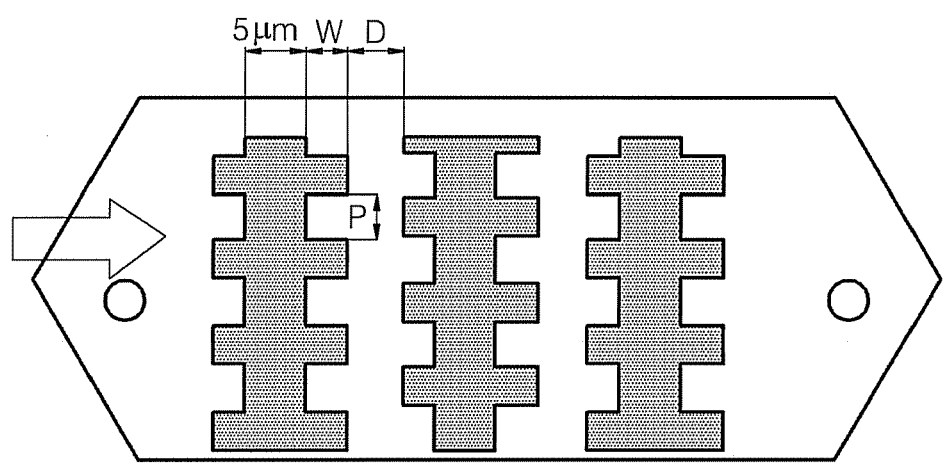
FIGS. 4 and 5A to 5D are diagrams illustrating the dimensions of an electrode portion used in an exemplary embodiment of the present invention.
Figure 5A:
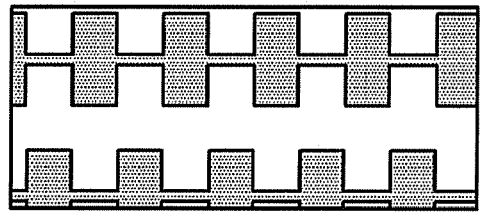
Figure 5B:
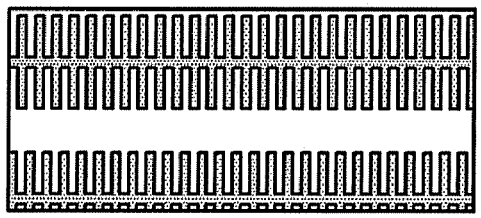
Figure 5C:
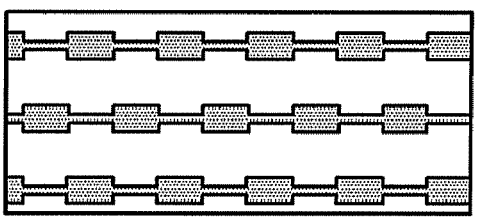
Figure 5D:
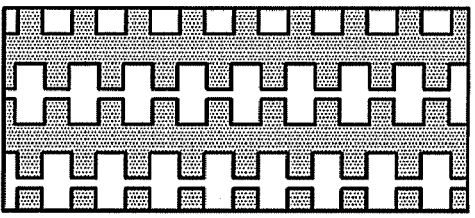

FIGS. 4 and 5 are diagrams illustrating dimensions of the electrode portion used in Example 1.

Referring to FIG. 4, the width of a metal line connecting gold pillars to metal pads was 5 μm. The distance between the gold pillars was P. The width of the gold pillars in the array of the gold posts was W. The distance between the gold pillars from one row of the gold pillars to the next was D. The arrow shows the direction of fluid flow.

All of the electrode structures illustrated in FIGS. 5A through 5D showed similar experiment results. Therefore, in the examples, experiments were performed with the microfluidic devices having the electrode dimension shown in FIG. 5A.

Figure 6:
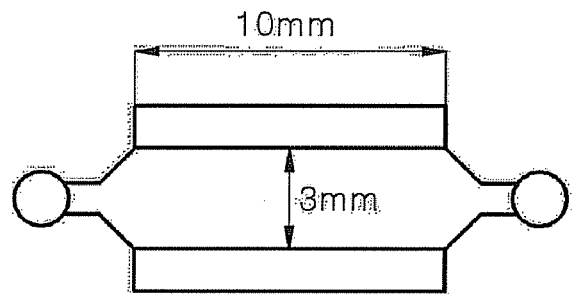
FIG. 6 is a cross-sectional view illustrating the dimensions of a reaction chamber used in an exemplary embodiment of the present invention.

FIG. 6 is a cross-sectional view illustrating the dimensions of an exemplary reaction chamber. Referring to FIG. 6, the reaction chamber had a length of 3 mm, a width of 10 mm and a volume of 4 μl.

Micro magnetic beads (e.g., Dynabeads MyOne™ Carboxylic Acid, DYNAL, Norway) were used as magnetic beads. A coin-shaped vibrating motor (e.g., DMJBRK 20 X, Samsung electro-mechanics, Republic of Korea) was used as a vibrating part. A high power laser, HLU 25 F 100-808 (e.g., LIMO, Germany), was used as a laser source.

EXAMPLE 2

<Cytolysis Efficiency According to Magnetic Bead Density>

Cytolysis efficiency according to magnetic bead density was investigated. Different quantities of beads were added to sample solutions (0 to $9\times10^6$ bead/μl) and a 1 W laser beam with an 808 nm wavelength was radiated on the sample solutions for 40 seconds. FIG. 7 is a graph illustrating the polymerase chain reaction ("PCR") results of DNA obtained from *E. coli* cells according to magnetic bead density. The crossing point ("Cp") refers to the number of cycles in the real-time PCR reaction required to obtain a detectable fluorescence signal. The higher the initial DNA density, the lower the Cp. Moreover, the Cp is related to DNA refinement. The higher the DNA purity, the lower the Cp. Therefore, the Cp is lower when the DNA of the sample solution is more refined.

Referring to FIG. 7, a higher density of the magnetic beads ensures that more DNA is obtained. High cytolysis efficiency was obtained and more DNA was extracted when the density of the magnetic beads was $5\times10^6$ bead/μl or greater. Moreover, the Cp value of *E. coli* DNA amplification for the exact measurement of the initial target copy number was investigated using LightCycler® ((e.g., Roche Diagnostics Corporation, IN, USA), a publicly known real-time PCR instrument. Referring to FIG. 7, the Cp value was reduced as the density of the magnetic beads increased. Thus, cytolysis efficiency increases as the density of magnetic beads increases.

EXAMPLE 3

<DEP Trapping Efficiency of Bacteria and Magnetic Beads According to Frequency of Applied Voltage>

Trapping efficiency according to the frequency of the applied voltage was investigated while flowing each of bacteria of *E. coli* (e.g., ATCC #11775), *Pseudomonas fluorescence* (e.g., ATCC #13525), *Streptococcus mutans* (e.g., ATCC #35668), and the magnetic beads of Example 1 through the reaction chamber.

Each kind of bacteria was flowed with a density of 107 cell/ml at a rate of 100 μl/min. The magnetic beads were flowed at a density of 105 bead/μl at a rate of 50 μl/min. The magnitude of the applied voltage was 20 V.

The results are shown in FIGS. 8A and 8B. FIG. 8A illustrates the trapping efficiency of each kind of bacteria according to the frequency of the applied voltage. FIG. 8B illustrates the trapping efficiency of magnetic beads according to the frequency of the applied voltage. Referring to FIGS. 8A and 8B, all of the bacteria and the magnetic beads showed optimum trapping efficiency at a frequency of between 100 kHz and 1 MHz. Therefore, both the bacteria and the magnetic beads can be captured under the same DEP conditions.

EXAMPLE 4

<Cell Trapping Efficiency According to Inflow Rate of Fluid>

The trapping efficiencies of *E. coli, Streptococcus mutans*, and *Staphylococcus epidermidis* were measured according to the inflow rate of fluid.

Bacteria which were not marked were used. The trapping efficiency was calculated as the eluted bacterial number, which was measured as the density (C output) of the solution that passed through a concentration chip to which an electric field was applied, divided by the injected bacterial number, which was measured as the density (C input) before flowing through the concentration chip.

Concentration ratio (times)=(density of eluted bacteria)/(density of input bacteria)

Two different methods were used to measure the density of cells: a colony count method was used for a density of 106 cell/ml or less and the cells were marked with fluorescence using a BacLight Bacterial viability kit (e.g., Molecular probes, U.S.) for a density of greater than 106 cell/ml. According to the manual of a product used, fluorescent labeling was performed by adding 3 μl of a staining mixture of SYPO 9 and propidium iodide to 1 ml of a cell solution. After 20 minutes, the fluorescent intensity was measured using a SpectraMax Gemini XS 20. To determine the relative quantity, a standard curve was obtained by performing serial dilution of a bacterium solution (OD600=1), and the density of the cell solution was measured relative to this standard curve. The absolute quantity of the bacterium solution (OD600=1) was measured using a colony count method by diluting the solution.

Figure 9:
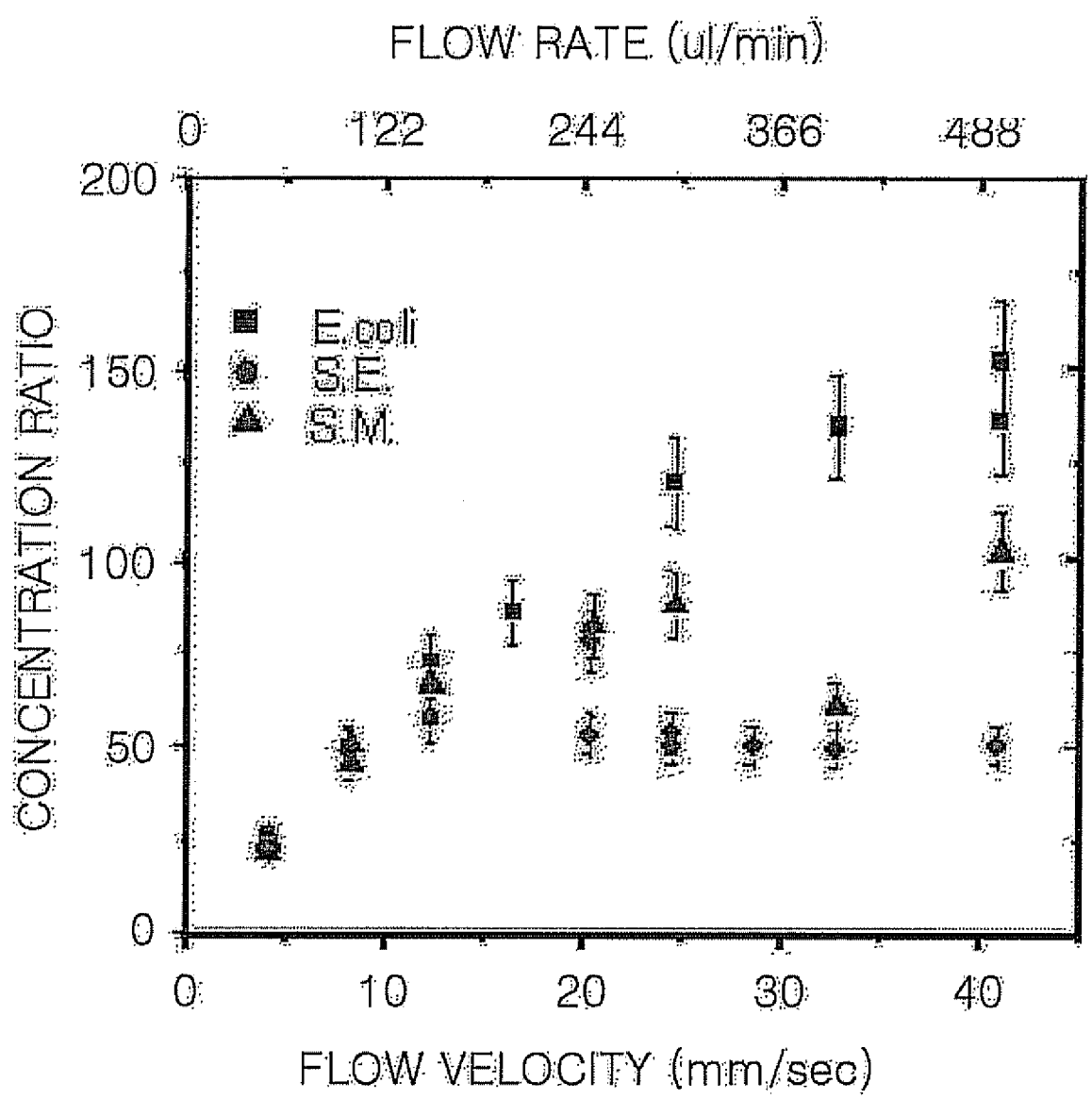
FIG. 9 is a graph illustrating concentration ratio according to inflow rate of a fluid.

FIG. 9 is a graph illustrating the concentration ratio according to the inflow rate of the fluid. In FIG. 9, the concentration ratio means (cell density of solution eluted with a 10 μl buffer after 2 minutes of capturing)/(initial cell density). Referring to FIG. 9, the higher the flow velocity, the higher the concentration ratio, and a maximum concentration ratio is obtained at a specific flow velocity.

EXAMPLE 5

<Trapping Efficiency of Magnetic Beads and Cells According to Capture Order>

The trapping efficiency according to the order in which the magnetic beads and the cells were captured was confirmed using the results obtained in Example 3. The voltage applied had a magnitude of 20 V and a frequency of 100 kHz.

After magnetic beads with a density of 105 bead/μl were flowed through a reaction chamber at a rate of 50 μl/min for one minute, *Streptococcus mutans* with a density of 107 cell/ml were flowed through at a rate of 250 μl/min for one minute.

FIG. 10A is a photograph taken after flowing magnetic beads through a reaction chamber at a rate of 50 μl/min for one minute. FIG. 10B is a photograph taken after flowing *Streptococcus mutans* at a rate of 250 μl/min for one second after flowing the magnetic beads through the reaction chamber. FIG. 10C is a photograph taken after flowing *Streptococcus mutans* at a rate of 250 μl/min for 60 seconds after flowing the magnetic beads through the reaction chamber.

Referring to FIG. 10A, magnetic beads were captured in the electrode portion by DEP. Referring to FIG. 10B, after further flowing bacteria at a rate of 250 μl/min for one second, some of the magnetic beads previously captured were released. Moreover, referring to FIG. 10C, after further flowing bacteria at a rate of 250 μl/min for 60 seconds, most of the magnetic beads previously captured were released due to the speed of the fluid.

From this result, it can be seen that capturing cells after capturing magnetic beads may not be desirable because the magnetic beads originally captured were released due to the high speed of the fluid.

After flowing the *Streptococcus mutans* with a density of $10^7$ cell/ml at a rate of 250 μl/min for four minutes, magnetic beads with a density of $10^5$ bead/μl were flowed at a rate of 50 μl/min for one minute, that is, in the opposite order to the experiment described above.

FIG. 11A is a photograph taken after flowing *Streptococcus mutans* at a rate of 250 μl/min for four minutes through the reaction chamber. FIG. 11B is a photograph taken after flowing magnetic beads at a rate of 50 μl/min for one minute after flowing the *Streptococcus mutans* through the reaction chamber. Referring to FIG. 11A, the bacteria were effectively captured in the electrode portion by DEP. Referring to FIG. 11B, magnetic beads were evenly and effectively captured between electrodes.

From this result, it can be seen that capturing magnetic beads after capturing cells is effective for capturing both magnetic beads and cells

EXAMPLE 6

<Confirmation of Cell Concentration Effect and Cytolysis Effect of Microfluidic Device According to an Exemplary Embodiment of Present Invention>

A PCR was performed in order to measure the quantity of DNA by using the microfluidic device of the present invention which has a reaction chamber of 4 μl using the following methods: a) performing cytolysis with a laser step after concentration using a chip for cell concentration in which a metal electrode is patterned; b) performing cytolysis with only a laser step and not a concentration step, using a chip for cell concentration in which a metal electrode is patterned on glass; and c) performing cytolysis with only a laser step and not a concentration step, using a cytolysis chip by a laser in which a silicon substrate is covered with a glass lid.

When a solution having a density of $10^7$ cell/ml and a bead concentration are mixed at ratio of 9:1 and put in the 4 μl reaction chamber, 36,000 cells exist in the reaction chamber. When a voltage is applied to the electrode of the chamber and the cells are concentrated, $10^6$ cells (concentration ratio: 28 times) exist if they flow at a rate of 100 μl/min for one minute: $2 \times 10^6$ cells (concentration ratio: 56 times) exist if they flow for two minutes, and $4 \times 10^6$ cells (concentration ratio: 111 times) exist if they flow for four minutes.

a) In order to confirm DNA quantity when performing both concentration using DEP and nucleic acid extraction using a laser, $10^7$ cell/ml (0.01 OD) of *Streptococcus mutans* was flowed at a rate of 100 μl/min while a voltage of 20 V with a frequency of 100 kHz was applied to an electrode. Next, $10^5$ bead/μl of magnetic beads were flowed at a rate of 50 μl/min for one minute, and then the voltage was removed. A 0.8 W laser was then radiated for 40 seconds. The magnetic beads were removed by flowing the solution out of the chamber. Then, PCR was performed by diluting 2 μl of the solution with water by a factor of 10. PCR was performed by a LightCycler® (e.g., Roche Diagnostics Corporation, IN, USA) using 20 μl of a reaction mixture including a 1× FastStart DNA Master SYBR (e.g., Roche Diagnostics Corporation, IN, USA), 0.25 mM forward and reverse primers (e.g., Genotech, Republic of Korea), 4 mM $MgCl_2$ (e.g., Roche Diagnostics Corporation), and D.W. (e.g., PCR class, Roche Diagnostics Corporation, IN, USA)

b) The DNA quantity was confirmed when performing only a nucleic acid extraction step using a laser in the same manner as described above, except that an electrode did not exist, a chip which bonds a glass lid to a silicon chip was used; cells and beads were supplied together; and the experiment was performed using cell concentrations of $10^7$ cell/ml (0.01 OD), $10^8$ cell/ml (0.1 OD) and $10^9$ cell/ml (1 OD).

c) A glass chip in which an Au electrode was patterned was used for cell concentration using DEP. All the experiment factors of the above method were used identically, except the followings: an electric field was not applied; beads and cells were supplied together; and it was performed on $10^7$ cell/ml (0.01 OD), $10^8$ cell/ml (0.1 OD) and $10^9$ cell/ml (1 OD) since a part in which Au was patterned could be barrier for laser penetration.

The results from the above cases are shown in Table 1 below and FIG. 12. As shown in Table 1 and FIG. 12, the amounts of DNA were similar in both cases b) and c). However, case c) had higher elution efficiency because the DEP chip had a smaller Cp for laser elution than a transparent chip. Moreover, when cell concentration was performed using a Au electrode with a DEP chip and a laser elution step was performed, the Cp value was smaller than when performing only laser elution without cell concentration. Therefore the amount of DNA was almost 111 times greater than expected.

TABLE 1

| | | Average of Cp | Standard deviation of Cp |
|---|---|---|---|
| DEP chip with Au electrode: performing laser elution after concentration (a) (triangles in FIG. 12) | (0.01 OD) | 14.82 | 0.07 |
| Chip used for laser elution (Si/glass bonded chip) (b) (squares in FIG. 12) | 1 OD | 16.73 | 0.16 |
| | 0.1 OD | 19.53 | 0.05 |
| | 0.01 OD | 21.55 | 0.18 |
| DEP chip with Au electrode: performing only laser elution without concentration (c) (circles in FIG. 12) | 1 OD | 16.01 | 0.02 |
| | 0.1 OD | 18.14 | 0.14 |
| | 0.01 OD | 21.32 | 0.31 |

As described above, when using the microfluidic device and the method of the present invention, cells or viruses can be effectively concentrated and lysed. Furthermore, the concentration and lysis of cells or viruses can be performed in a single chamber. Therefore, the size of an LOC can be reduced using the microfluidic device and the method according to the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic device for concentration and lysis of cells or viruses comprising:
    magnetic beads;
    a reaction chamber in which the magnetic beads are accommodated, the reaction chamber comprising a plurality of electrodes crossing each other and separated by a dielectric to generate an electric field;
    a laser source which radiates a laser onto the magnetic beads in the reaction chamber;
    at least two metal pads; and
    a plurality of metal lines respectively connected to the at least two metal pads,
    wherein the plurality of electrodes comprise at least two rows of electrodes each of the at least two rows being arranged substantially perpendicular to fluid flow, odd rows respectively being connected to one of the at least two metal pads through metal lines of the plurality of metal lines and even rows respectively being connected to another of the at least two metal pads through the remaining metal lines of the plurality of metal lines.

2. The microfluidic device of claim 1, further comprising a vibrating part agitating the magnetic beads in the reaction chamber.

3. The microfluidic device of claim 1, wherein the size of the magnetic beads is about 50 nm to about 1,000 μm.

4. The microfluidic device of claim 1, wherein the size of the magnetic beads is about 1 μm to about 50 μm.

5. The microfluidic device of claim 3, wherein the magnetic beads are a mixture of magnetic beads of two or more different sizes.

6. The microfluidic device of claim 1, wherein the magnetic beads comprise one or more materials selected from the group consisting of Fe, Ni and Cr, and oxides thereof.

7. The microfluidic device of claim 1, wherein the magnetic beads comprise ferromagnetic metals coated on a polymer, an organic material, silicon, or glass.

8. The microfluidic device of claim 1, wherein the magnetic beads comprise a surface functional group which is hydrophilic and negatively charged.

9. The microfluidic device of claim 8, wherein the surface functional group of the magnetic beads is a carboxy radical or a derivative thereof.

10. The microfluidic device of claim 1, wherein the electrodes of the odd rows overlap neighboring electrodes of the even rows.

11. The microfluidic device of claim 1, wherein the electrodes of each of the odd rows are connected to the one of the metal pads through the same metal line, and the electrodes of each of the even rows are connected to the other of the metal pads through the same metal line.

12. The microfluidic device of claim 1, wherein the interval between one of the electrodes of one of the odd rows and the neighboring electrode of the neighboring even row is about 10 μm to about 100 μm, the interval between adjacent electrodes within the odd rows and the even rows is about 10 μm to about 100 μm, and the height of the electrodes is about 0.1 μm to about 100 μm.

13. The microfluidic device of claim 1, wherein the electrodes are columnar.

14. The microfluidic device of claim 1, wherein the electrodes are flat.

15. The microfluidic device of claim 1, wherein the angle between the electrode and a substrate to which the electrode is adhered is from about 50° to about 120°.

16. The microfluidic device of claim 1, wherein the electrodes are composed of gold coated on a metal.

17. The microfluidic device of claim 16, wherein the metal is nickel.

18. The microfluidic device of claim 1, wherein the chamber comprises a lower substrate and an upper substrate, and the electrodes are disposed on at least one of the lower substrate and the upper substrate.

19. The microfluidic device of claim 1, wherein the chamber comprises a lower substrate and an upper substrate, and the electrodes are disposed on the lower substrate and on the upper substrate, rows of the electrodes disposed on the lower substrate and rows of the electrodes disposed on the upper substrate correspond to each other, the electrodes of odd rows of the lower substrate and the electrodes of the even rows of upper substrate are connected to the same metal pad, and the electrodes of even rows of the lower substrate and the electrodes of odd rows of the upper substrate are connected to the same metal pad.

20. The microfluidic device of claim 2, wherein the vibrating part is selected from the group consisting of:
    an ultrasonic cleaner;
    a vibrating part using a magnetic field;
    a vibrating part using an electric field;
    a mechanical vibrating unit; and
    a piezoelectric material.

21. The microfluidic device of claim 1, wherein the laser source is a pulse laser or a continuous wave laser.

22. The microfluidic device of claim 21, wherein the pulse laser output power is more than 1 mJ/pulse and the continuous laser output power is more than 10 mW.

23. The microfluidic device of claim 21, wherein the laser generates light in a wavelength band of 400 nm or greater.

24. The microfluidic device of claim 1, wherein the reaction chamber is a single chamber.

25. The microfluidic device of claim 1, further comprising at least one of a plurality of metal plates and a plurality of metal posts which extend from the plurality of metal lines in a direction substantially perpendicular to fluid flow.

* * * * *